US012806214B2

(12) United States Patent
Fusaro et al.

(10) Patent No.: US 12,806,214 B2
(45) Date of Patent: Nov. 24, 2026

(54) METHODS OF TREATING BACTERIAL INFECTIONS WITH MINOCYCLINE

(71) Applicant: MELINTA SUBSIDIARY CORP., Parsippany, NJ (US)

(72) Inventors: Karen Fusaro, Summit, NJ (US); David C. Griffith, San Marcos, CA (US); Jeffrey S. Loutit, Los Altos, CA (US)

(73) Assignee: MELINTA SUBSIDIARY CORP., Parsippany, NJ (US)

( * ) Notice: Subject to any disclaimer, the term of this patent is extended or adjusted under 35 U.S.C. 154(b) by 642 days.

(21) Appl. No.: 17/052,141

(22) PCT Filed: Apr. 26, 2019

(86) PCT No.: PCT/US2019/029271
§ 371 (c)(1),
(2) Date: Oct. 30, 2020

(87) PCT Pub. No.: WO2019/212883
PCT Pub. Date: Nov. 7, 2019

(65) Prior Publication Data

US 2021/0052608 A1 Feb. 25, 2021

Related U.S. Application Data

(60) Provisional application No. 62/730,993, filed on Sep. 13, 2018, provisional application No. 62/664,884, filed on Apr. 30, 2018.

(51) Int. Cl.

| | |
|---|---|
| ***A61K 31/65*** | (2006.01) |
| ***A61K 9/00*** | (2006.01) |
| ***A61P 31/04*** | (2006.01) |

(52) U.S. Cl.
CPC ............ *A61K 31/65* (2013.01); *A61K 9/0019* (2013.01); *A61P 31/04* (2018.01)

(58) Field of Classification Search
CPC ........ A61K 31/65; A61K 9/0019; A61P 31/04
See application file for complete search history.

(56) References Cited

U.S. PATENT DOCUMENTS

| | | | |
|---|---|---|---|
| 3,335,055 | A | 8/1967 | Weidenheimer |
| 3,674,859 | A | 7/1972 | Beutel et al. |
| 3,846,548 | A | 11/1974 | Akazawa et al. |
| 3,957,980 | A | 5/1976 | Noseworthy |
| 4,701,320 | A | 10/1987 | Hasegawa et al. |
| 5,348,748 | A | 9/1994 | Sheth et al. |
| 6,884,784 | B1 | 4/2005 | Mitchell et al. |
| 7,879,828 | B2 | 2/2011 | Fawzi et al. |
| 9,084,802 | B2 | 7/2015 | Griffith et al. |
| 9,278,105 | B2 | 3/2016 | Griffith et al. |
| 11,944,634 | B2 | 4/2024 | Griffith et al. |
| 12,161,656 | B2 | 12/2024 | Griffith et al. |
| 2004/0014750 | A1 | 1/2004 | Michaelis et al. |
| 2005/0038002 | A1 | 2/2005 | Nelson et al. |
| 2006/0183719 | A1 | 8/2006 | deVries et al. |
| 2007/0243244 | A1 | 10/2007 | Shah et al. |
| 2008/0233206 | A1 | 9/2008 | Chomczynski |
| 2014/0274969 | A1 | 9/2014 | Casha et al. |
| 2017/0333455 | A1 | 11/2017 | Manley et al. |

FOREIGN PATENT DOCUMENTS

| | | | | | |
|---|---|---|---|---|---|
| CN | 101301268 | A | 11/2008 | | |
| EP | 0337733 | A2 | 10/1989 | | |
| GB | 901107 | A | 7/1962 | | |
| GB | 1131007 | A | 10/1968 | | |
| WO | WO-2009/155931 | A1 | 12/2009 | | |
| WO | WO-2010/033800 | A2 | 3/2010 | | |
| WO | WO-2016154332 | A1 * | 9/2016 | ............. | A61K 31/65 |
| WO | WO-2017192516 | A1 * | 11/2017 | ............. | A61K 31/65 |
| WO | WO-18/129463 | A1 | 7/2018 | | |
| WO | WO-19/0212883 | A1 | 11/2019 | | |

OTHER PUBLICATIONS

J. Lashinsky et al.. Minocycline for the Treatment of Multidrug and Extensively Drug-Resistant A. baumannii: A Review. Infect Dis Ther. Jun. 2017;6(2):199-211. doi: 10.1007/s40121-017-0153-2. Epub Mar. 29, 2017. PMID: 28357705; PMCID: PMC5446366. (Year : 2017).*

W. Alfouzan, et al. (Pharmacodynamics of minocycline against Acinetobacter baumannii studied in a pharmacokinetic model of infection, International Journal of Antimicrobial Agents, vol. 50, Issue 6, 2017, pp. 715-717, ISSN 0924-8579, https://doi.org/10.1016/j.ijantimicag.2017.06.026. (Year: 2017).*

J. Lashinsky et al. (Minocycline for the Treatment of Multidrug and Extensively Drug-Resistant A. baumannii: A Review. Infect Dis Ther. Jun. 2017;6(2):199-211. doi: 10.1007/s40121-017-0153-2. (Year: 2017).*

David J. Ritchie, Clinical Infectious Diseases, vol. 59, Issue suppl_6, Dec. 2014, pp. S374-S380. (Year: 2014).*

H. Macdonald, et al., Clinical Pharmacology & Therapeutics, 1973, 14, doi: 10.1002/cpt1973145852. (Year: 1973).*

Office Action issued Mar. 15, 2023 by China National Intellectual Property Administration in Chinese Patent Application No. 201980037125.2 with English translation (6 total pages).

Lashinsky, J.N., et al., "Minocycline for the Treatment of Multidrug and Extensively Drug-Resistant A. baumannii: A Review," Infect. Dis. Ther., vol. 6, pp. 199-211 (Mar. 29, 2017).

Cornely, O.A., et al., "Phase I Study to Evaluate the Safety and Pharmacokinetics of Single and Multiple Ascending Doses of Intravenous Minocycline in Healthy Adult Subjects," Poster presented at IDWeek 2018 in San Francisco, CA on Oct. 3-7, 2018 (1 total page).

Fagan, S.C., et al., "Minocycline to Improve Neurologic Outcome in Stroke (MINOS): A Dose-Finding Study," Stroke, 41(10): 2283-2287, Oct. 2010, Author Manuscript available in PMC Feb. 6, 2014 (11 total pages).

Casha, S., et al., "Results of a phase II placebo-controlled randomized trial of minocycline in acute spinal cord injury," Brain—A Journal of Neurology, vol. 135, pp. 1224-1236 (Feb. 2012).

(Continued)

*Primary Examiner* — James H Alstrum-Acevedo
*Assistant Examiner* — Manahil Mirghani Ali Abdalhameed
(74) *Attorney, Agent, or Firm* — Wilmer Cutler Pickering Hale and Dorr LLP

(57) ABSTRACT

Disclosed herein are methods of treating carbapenem-resistant bacterial infections in a subject using various dosages of minocycline.

11 Claims, 2 Drawing Sheets

(56) References Cited

OTHER PUBLICATIONS

International Search Report and Written Opinion mailed Jul. 30, 2019 by U.S. Patent and Trademark Office as International Searching Authority for International Patent App. No. PCT/US019/029271 (10 total pages).
Ritchie, D.J. and Garavaglia-Wilson, A., "A Review of Intravenous Minocycline for Treatment of Multigrug-Resistant Acinetobacter Infections," Clinical Infectious Diseases, vol. 59, Suppl. 6, pp. S374-S380 (2014).
Greig, S. L. and Scott, L.J., "Intravenous Minocycline: A Review in Acinetobacter Infections," Drugs, vol. 76, pp. 1467-1476 (published online Aug. 30, 2016).
Pogue, J.M., et al., "Carbapenem-Resistance in Gram-Negative Bacilli and Intravenous Minocycline: An Antimicrobial Stewardship Approach at the Detroit Medical Center," Clinical Infectious Diseases, vol. 59, Suppl. 6, pp. S388-S393 (2014).
No Author, "History of Changes for Study: NCT02802631—Study to Evaluate Safety, Tolerability, and Pharmacokinects of Minocin® (Minocycline) for Injection in Health," ClinicalTrials.gov: Archive: Mar. 1, 2018, last retrieved Dec. 6, 2021 from URL: https://www.clinicaltrials.gov/ct2/history/NCT02802631?V_8=View#StudyPageTop (5 total pages).
Extended European Search Report issued by European Patent Office on Dec. 21, 2021 for European Patent Application No. 19796660.9 (9 total pages).
Office Action mailed Nov. 29, 2022 by Mexican Patent Office in Mexican Patent Application No. MX/a/2020/011599 with English translation (12 total pages).
Communication pursuant to Article 94(3) EPC mailed Jan. 30, 2023 by European Patent Office in European Patent Application No. 19796660.9 (10 total pages).
Office Action mailed May 24, 2023 by Mexican Patent Office in Mexican Patent Application No. MX/a/2020/011599 with English translation (14 total pages).
Summons to attend oral proceedings pursuant to Rule 115(1) EPC issued Jan. 25, 2024 by European Patent Office in European Patent Application No. 19796660.9 (10 total pages).
Office Action issued Mar. 7, 2024 by Canadian Intellectual Property Office in Canadian Patent Application No. 3098302 (7 total pages).
Coppoc, G.L., "Tetracycline Antibiotics," Copyright, Purdue Research Foundation, 8 total pages (1996).
Eagle, H. and Brewer, G., "Mechanism of Hemolysis by Complement: I. Complement Fixation as an Essential Preliminary to Hemolysis," J. Gen. Physiol., pp. 845-862 (Accepted for publication Mar. 16, 1929).
Gonzalez, A.J., et al., Effect of Intravenous Magnesium Sulfate on Chronic Obstructive Pulmonary disease exacerbations requiring Hospitalizations: A Randomized Placebo-Controlled Trial, Arch. Broncoenumol., vol. 42, No. 10, p. 491 (Oct. 2006).
Berthon. G., et al., "Metal Ion-Tetracycline Interactions in Biological Fluids: 2. Potentiometric Study of Magnesium Complexes with Tetracycline, Oxytetracycline, Doxycycline, and Minocycline, and Discussion of their Possible Influence on the Bioavailability of these Antibiotics in Blood Plasma," Journal of Inorganic Biochemistry, vol. 19, pp. 1-18 (1983).
NDA Label for Minocin—Minocycline Hydrochloride Oral Suspension (NDA 50-444/S-045 and NDA 50-445/S-027), Triax Pharmaceuticals, LLC Manufactured for Triax Pharmaceuticals, LLC by Wyeth Pharmaceuticals, Inc., pp. 18-32 (Revised Oct. 2006).
NDA Label for Minocin—Minocycline For Injection 100 Mg/Vial Intravenous (NDA 50-444/S-045 and NDA 50-445/S-027), Triax Pharmaceuticals, LLC Manufactured for Triax Pharmaceuticals, LLC by Wyeth Pharmaceuticals, Inc., pp. 3-17 (Revised Oct. 2006).
TRIAX Pharmaceuticals, LLC, Minocin® Minocycline For Injection 100 Mg/Vial Intravenous, Aug. 2010, pp. 3-19, Document No. NDA 50-444/S-047.
Pawelczyk, E. and Matlak, B., "Kinetics Drug Decomposition: Part 74. Kinetics of Degradation of Minocycline in Aqueous Solution," Pol. J. Pharmacol. Pharm., vol. 34, pp. 409-421 (1982).
Zakai et al., "Prevention of Hemolysis by Bivalent Metal Ions During Virus-Induced Fusion of Erythrocytes With Ehrlich Ascites Tumor Cells," FEBS Letters, vol. 40, No. 2, pp. 331-334 (Apr. 1974).

* cited by examiner

METHODS OF TREATING BACTERIAL INFECTIONS WITH MINOCYCLINE

This application is a National Stage Entry of PCT International Application No. PCT/US2019/029271 filed Apr. 26, 2019, which claims the benefit of and priority under 35 U.S.C. § 119(e) to U.S. Ser. No. 62/664,884 filed Apr. 30, 2018, and U.S. Ser. No. 62/730,993 filed Sep. 13, 2018, the contents of which are hereby incorporated by reference in their entirety.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All patents, patent applications and publications cited herein are hereby incorporated by reference in their entirety. The disclosure of these publications in their entireties are hereby incorporated by reference into this application in order to more fully describe the state of the art as known to those skilled therein as of the date of the invention described herein.

BACKGROUND OF THE INVENTION

The present disclosure relates to antimicrobial compounds, compositions, their use and preparation as therapeutic agents, and methods of treating various bacterial infections.

DESCRIPTION OF THE RELATED TECHNOLOGY

Bacterial infections are contagious and may result in many serious or life-threatening complications. Antibiotics have been effective tools in combating bacterial infections for during the last half-century. Some bacterial infections are particularly problematic and resistant to treatment. Gram-negative bacteria cause infections including pneumonia, bloodstream infections, and wound infections. However, many gram-negative bacteria are resistant to antibiotics available on the market and present significant risks to patients, particularly at high doses.

Carbapenem-resistant Enterobacteriaceae are Gram-negative bacteria that are resistant to the carbapenem class of antibiotics, which are considered the drugs of last resort for such infections. The prognosis of CRE infections ranges from fair to poor; the bacteria can kill up to half of patients who get bloodstream infections. Carbapenem-resistant *Acinetobacter baumannii* infections are considered a critical threat by the World Health Organization.

Intravenous minocycline is approved in the United States for treatment of *Acinetobacter* infections at doses of up to 200 mg administered twice daily. However, it is desirable to identify a range of safe dosages and dosing regimens for minocycline in adult subjects in order to increase treatment efficacy.

SUMMARY OF THE INVENTION

Some embodiments of the present disclosure relate to methods of treating one or more bacterial infection in a subject, wherein the infection is carbapenem-resistant, comprising administering minocycline to the subject in need thereof at a dose of greater than 200 mg.

In some embodiments, the bacterial infection may be selected from the group consisting of *Escherichia coli, Klebsiella pneumoniae, Pseudomonas aeruginosa, Enterobacter cloacae* species complex, *Enterococcus faecium, Serratia marcescens. Streptococcus pyogenes, Streptococcus pneumoniae, Haemophilus influenzae. Chlamydia trachomatis. Mycoplasma pneumoniae, Legionella pneumophila, Acinetobacter baumannii, Bartonella bacilliformis, Brucella* species, *Calymmatobacterium granulomatis. Campylobacter fetus, Francisella tularensis, Haemophilus dicreyi, Vibrio cholerae*, and *Yersinia pestis*. In some specific embodiments, the bacterial infection can be *Acinetobacter baumannii.*

In some embodiments, the administration of minocycline may be oral, intravenous, intraperitoneal, intragastric, or intravascular administration. In some specific embodiments, the administration of minocycline is intravenous administration.

In some embodiments, the dose of the minocycline administered may be from about 250 mg to about 1000 mg. In some embodiments, the dose of minocycline may be at least about 300 mg. In some embodiments, the dose of minocycline may be at least about 400 mg. In some embodiments, the dose of minocycline may be at least about 500 mg. In some embodiments, the dose of minocycline may be at least about 600 mg.

In some embodiments, the dose of minocycline may be administered from one to four times daily. In some embodiments, the dose of minocycline may be administered one time daily. In some embodiments, the dose of minocycline may be administered two times daily. In some embodiments, the dose of minocycline is administered three times daily.

In some embodiments, an initial loading dose of about 600 mg minocycline may be administered. In some embodiments, dose of from about 100 mg to about 600 mg minocycline may be administered twice daily after the initial loading dose of 600 mg minocycline.

In some embodiments, the minocycline may be administered from about 1 day to at least about 4 weeks.

BRIEF DESCRIPTION OF THE FIGURES

To conform to the requirements for PCT patent applications, the figures presented herein are black and white representations of images originally created in color.

DETAILED DESCRIPTION OF THE INVENTION

Figure 1:
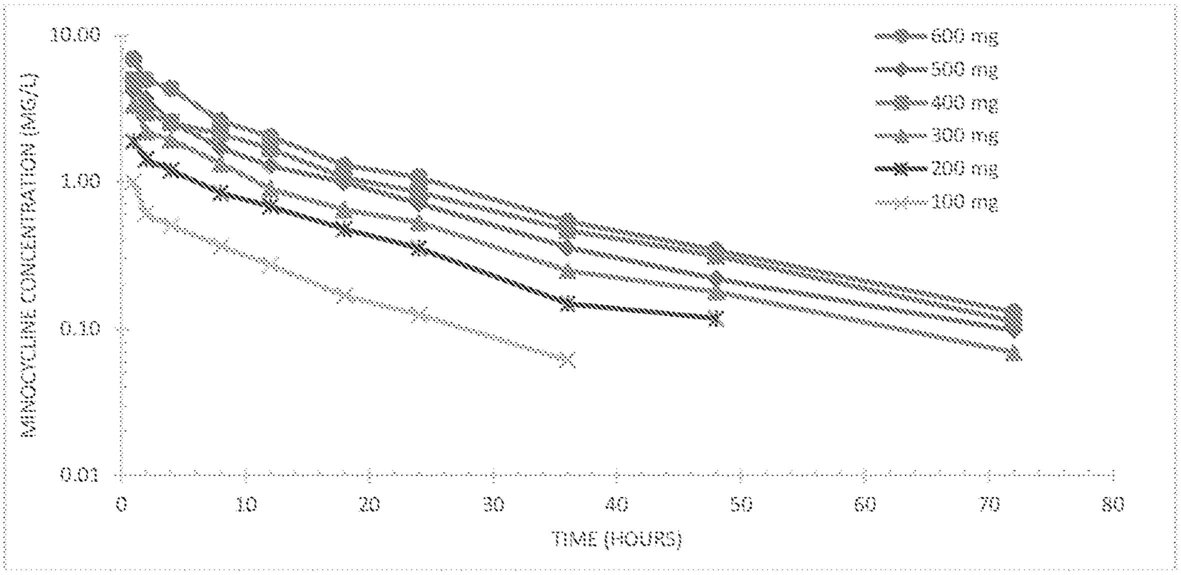
FIG. 1 shows plasma pharmacokinetics of minocycline in healthy volunteers after a 1 hour intravenous Infusion.

Some embodiments of the present disclosure relate to methods of treating one or more bacterial infection in a subject, wherein the infection is carbapenem-resistant, comprising administering minocycline to the subject in need thereof at a dose of greater than 200 mg.

In some embodiments, the bacterial infection may be selected from the group consisting of *Escherichia coli, Klebsiella pneumoniae. Pseudomonas aeruginosa, Enterobacter cloacae* species complex, *Enterococcus faecium, Serratia marcescens. Streptococcus pyogenes. Streptococcus pneumoniae, Haemophilus influenzae. Chlamydia trachomatis. Mycoplasma pneumoniae. Legionella pneumophila, Acinetobacter baumannii, Bartonella bacilliformis,*

*Brucella* species, *Calymmatobacterium granulomatis*. *Campylobacter fetus, Francisella tularensis, Haemophilus dicreyi, Vibrio cholerae*, and *Yersinia pestis*. In some specific embodiments, the bacterial infection can be *Acinetobacter baumannii*.

In some embodiments, the administration of minocycline may be oral, intravenous, intraperitoneal, intragastric, or intravascular administration. In some specific embodiments, the administration of minocycline is intravenous administration.

In some embodiments, the dose of the minocycline administered may be from about 250 mg to about 1000 mg. In some embodiments, the dose of minocycline may be at least about 300 mg. In some embodiments, the dose of minocycline may be at least about 400 mg. In some embodiments, the dose of minocycline may be at least about 500 mg. In some embodiments, the dose of minocycline may be at least about 600 mg.

In some embodiments, the dose of minocycline may be administered from one to four times daily. In some embodiments, the dose of minocycline may be administered one time daily. In some embodiments, the dose of minocycline may be administered two times daily. In some embodiments, the dose of minocycline is administered three times daily.

In some embodiments, an initial loading dose of about 600 mg minocycline may be administered. In some embodiments, dose of from about 100 mg to about 600 mg minocycline may be administered twice daily after the initial loading dose of 600 mg minocycline.

In some embodiments, the minocycline may be administered from about 1 day to at least about 4 weeks.

Definitions

As used herein, a "subject" refers to an animal that is the object of treatment, observation or experiment. "Animal" includes cold- and warm-blooded vertebrates and invertebrates such as fish, shellfish, reptiles, and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional, such as a Medical Doctor (i.e. Doctor of Allopathic medicine or Doctor of Osteopathic medicine) or a Doctor of Veterinary Medicine, to attempt to cure, or at least ameliorate the effects of, a particular disease or disorder or to prevent the disease or disorder from occurring in the first place.

As used herein, "treat," "treatment," or "treating" refers to administering a pharmaceutical composition for prophylactic and/or therapeutic purposes. The term "prophylactic treatment" refers to treating a patient who does not yet have the relevant disease or disorder, but who is susceptible to, or otherwise at risk of, a particular disease or disorder, whereby the treatment reduces the likelihood that the patient will develop the disease or disorder. The term "therapeutic treatment" refers to administering treatment to a patient already having a disease or disorder.

As used herein, "administration" or "administering" refers to a method of giving a dosage of a pharmaceutically active ingredient to a vertebrate.

As used herein, a "dosage" refers to an amount of therapeutic agent administered to a patient.

As used herein, a "daily dosage" refers to the total amount of therapeutic agent administered to a patient in a day.

As used herein, the term "therapeutic agent" means a substance that is effective in the treatment of a disease or condition.

As used herein, "therapeutically effective amount" or "pharmaceutically effective amount" is meant an amount of therapeutic agent, which has a therapeutic effect. The dosages of a pharmaceutically active ingredient which are useful in treatment are therapeutically effective amounts. Thus, as used herein, a therapeutically effective amount means those amounts of therapeutic agent which produce the desired therapeutic effect as judged by clinical trial results and/or model animal studies.

As used herein, a "therapeutic effect" relieves, to some extent, one or more of the symptoms of a disease or disorder. For example, a therapeutic effect may be observed by a reduction of the subjective discomfort that is communicated by a subject (e.g., reduced discomfort noted in self-administered patient questionnaire).

Treatment of Bacterial Infection

In one aspect, the present disclosure relates to the treatment of a subject that may be suffering from one or more bacterial infections. In some embodiments, the subject may be infected with a gram-negative bacteria. In one embodiment, the subject may be infected with *Escherichia coli*. In one embodiment, the subject may be infected with *Klebsiella pneumoniae*. In one embodiment, the subject may be infected with *Pseudomonas aeruginosa*. In one embodiment, the subject may be infected with *Enterobacter cloacae* species complex. In one embodiment, the subject may be infected with *Enterococcus faecium*. In one embodiment, the subject may be infected with *Serratia marcescens*. In one embodiment, the subject may be infected with *Streptococcus pyogenes*. In one embodiment, the subject may be infected with *Streptococcus pneumoniae*. In one embodiment, the subject may be infected with *Haemophilus influenzae*. In one embodiment, the subject may be infected with *Chlamydia trachomatis*. In one embodiment, the subject may be infected with *Mycoplasma pneumoniae*. In one embodiment, the subject may be infected with *Legionella pneumophila*. In one embodiment, the subject may be infected with *Acinetobacter baumannii*. In one embodiment, the subject may be infected with *Bartonella bacilliformis*. In one embodiment, the subject may be infected with *Brucella* species. In one embodiment, the subject may be infected with *Calymmatobacterium granulomatis*. In one embodiment, the subject may be infected with *Campylobacter fetus*. In one embodiment, the subject may be infected with *Francisella tularensis*. In one embodiment, the subject may be infected with *Haemophilus ducreyi*. In one embodiment, the subject may be infected with *Vibrio cholerae*. In one embodiment, the subject may be infected with *Yersinia pestis*.

Pharmaceutical Compositions

In another aspect, the present disclosure relates to a pharmaceutical composition comprising a physiologically acceptable surface active agents, carriers, diluents, excipients, smoothing agents, suspension agents, film forming substances, and coating assistants, or a combination thereof; and a compound disclosed herein. Acceptable carriers or diluents for therapeutic use are well known in the pharmaceutical art, and are described, for example, in Remington's Pharmaceutical Sciences, 18th Ed., Mack Publishing Co., Easton, PA (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The minocycline can be formulated for administration with a pharmaceutically acceptable carrier or diluent. The minocycline can be formulated as a medicament with a standard pharmaceutically acceptable carrier(s) and/or excipient(s) as is routine in the pharmaceutical art. The exact nature of the formulation will depend upon several factors including the desired route of administration. Typically, minocycline are formulated for oral, inhalation, intravenous, intragastric, intravascular or intraperitoneal administration.

The term "pharmaceutical composition" refers to a mixture of a compound or compounds disclosed herein with other chemical components, such as diluents or carriers. The pharmaceutical composition facilitates administration of the compound(s) to an organism. Multiple techniques of administering a compound exist in the art including, but not limited to, oral, injection, aerosol, parenteral, and topical administration. Pharmaceutical compositions can also be obtained by reacting compound(s) with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines a chemical compound diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compound or combination of compounds disclosed herein may be found in "Remington's Pharmaceutical Sciences," Mack Publishing Co., Easton, PA, 18th edition, 1990.

Some embodiments provide the compound(s) or combination of compounds disclosed herein in tablets, film coated tablets, capsules, caplets, pills, gel caps, pellets, beads, or dragée dosage forms. Preferably, the formulations disclosed herein can provide favorable drug processing qualities, including, for example, but not limited to, rapid tablet press speeds, reduced compression force, reduced ejection forces, blend uniformity, content uniformity, uniform dispersal of color, accelerated disintegration time, rapid dissolution, low friability (preferable for downstream processing such as packaging, shipping, pick-and-pack, etc.) and dosage form physical characteristics (e.g., weight, hardness, thickness, friability) with little variation.

The compound(s) or combination of compounds disclosed herein can be formulated readily, for example, by combining the drug substance with any suitable pharmaceutically acceptable excipient(s) for example, but not limited to, binders, diluents, disintegrants, lubricants, fillers, carriers, coatings, glidants, flavors, color additives, and the like, as set forth below. Such compositions can be prepared for storage and for subsequent processing.

Excipients

Acceptable excipients for therapeutic use are well known in the pharmaceutical art, and are described, for example, in Handbook of Pharmaceutical Excipients, 5th edition (Raymond C Rowe, Paul J Sheskey and Siân C Owen, eds. 2005), and Remington: The Science and Practice of Pharmacy, 21st edition (Lippincott Williams & Wilkins, 2005), each of which is hereby incorporated in its entirety. The term "carrier" material or "excipient" herein can mean any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule, tablet, film coated tablet, caplet, gel cap, pill, pellet, bead, and the like suitable for oral administration. Excipients can include, by way of illustration and not limitation, diluents, disintegrants, binding agents, wetting agents, polymers, lubricants, glidants, coatings, sweetens, solubilizing agents, substances added to mask or counteract a disagreeable taste or odor, flavors, colorants, fragrances, and substances added to improve appearance of the composition.

The compositions and formulations can include any other agents that provide improved transfer, delivery, tolerance, and the like. These compositions and formulations can include, for example, powders, pastes, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax.

Any of the foregoing mixtures can be appropriate in treatments and therapies in accordance with the disclosure herein, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol. Pharmacol. 32(2):210-8 (2000), Charman W N "Lipids, lipophilic drugs, and oral drug delivery-some emerging concepts." J. Pharm. Sci. 89(8):967-78 (2000), and the citations therein for additional information related to formulations, excipients and carriers well known to pharmaceutical chemists.

In some embodiments, one or more, or any combination of the listed excipients can be specifically included or excluded from the formulations and/or methods disclosed herein. As will be appreciated by those of skill in the art, the amounts of excipients will be determined by drug dosage and dosage form size.

Lubricants

In some embodiments, lubricants are employed in the manufacture of certain dosage forms. For example, a lubricant will often be employed when producing tablets. In some embodiments, a lubricant can be added just before the tableting step, and can be mixed with the formulation for a minimum period of time to obtain good dispersal. In some embodiments, one or more lubricants can be used. Examples of suitable lubricants include, but are not limited to, magnesium stearate, calcium stearate, zinc stearate, stearic acid, talc, glyceryl behenate, polyethylene glycol, polyethylene oxide polymers (for example, available under the registered trademarks of Carbowax® for polyethylene glycol and Polyox® for polyethylene oxide from Dow Chemical Company, Midland, Mich.), sodium lauryl sulfate, magnesium lauryl sulfate, sodium oleate, sodium stearyl fumarate, DL-leucine, colloidal silica, and others as known in the art. Typical lubricants are magnesium stearate, calcium stearate, zinc stearate and mixtures of magnesium stearate with sodium lauryl sulfate.

Color Additives

In some embodiments, color additives also can be included. The colorants can be used in amounts sufficient to distinguish dosage form strengths. Preferably, color additives approved for use in drugs (21 CFR 74, which is incorporated herein by reference in its entirety) are added to the commercial formulations to differentiate tablet strengths. The use of other pharmaceutically acceptable colorants and combinations thereof are encompassed by the current disclosure.

Binders

Binders can be used, for example, to impart cohesive qualities to a formulation, and thus ensure that the resulting dosage form remains intact after compaction. Suitable binder materials include, but are not limited to, microcrystalline cellulose, gelatin, sugars (including, for example, sucrose, glucose, dextrose and maltodextrin), polyethylene glycol, waxes, natural and synthetic gums, polyvinylpyrrolidone, pregelatinized starch, povidone, cellulosic polymers (including, for example, hydroxypropyl cellulose (HPC), hydroxypropyl methylcellulose (HPMC), methyl cellulose, hydroxyethyl cellulose, and the like), hydroxypropyl cellulose (HPC), and the like. Accordingly, in some embodiments, the formulations disclosed herein can include at least one binder to enhance the compressibility of the major excipient(s). In some embodiments, the binder(s) is(are) sprayed on from solution, e.g. wet granulation, to increase binding activity.

Disintegrants

In some embodiments, disintegrants are used, for example, to facilitate tablet disintegration after administration, and are generally starches, clays, celluloses, algins, gums, or crosslinked polymers. Suitable disintegrants include, but are not limited to, crosslinked polyvinylpyrrolidone (PVP-XL), sodium starch glycolate, alginic acid, methacrylic acid DYB, microcrystalline cellulose, crospovidone, polacriline potassium, sodium starch glycolate, starch, pregelatinized starch, croscarmellose sodium, and the like. If desired, the pharmaceutical formulation can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, sodium lauryl sulfate, dioctyl sodium sulfosuccinate, polyoxyethylene sorbitan fatty acid esters, etc. and the like.

Coatings

In some embodiments, the formulations can include a coating, for example, a film coating. Where film coatings are involved, coating preparations can include, for example, a film-forming polymer, a plasticizer, or the like. Also, the coatings can include pigments and/or opacifiers. Non-limiting examples of film-forming polymers include hydroxypropyl methylcellulose, hydroxypropyl cellulose, methylcellulose, polyvinyl pyrrolidine, and starches. Non-limiting examples of plasticizers include polyethylene glycol, tributyl citrate, dibutyl sebecate, castor oil, and acetylated monoglyceride. Furthermore, non-limiting examples of pigments and opacifiers include iron oxides of various colors, lake dyes of many colors, titanium dioxide, and the like.

Diluents

In some embodiments, diluents are used, and are generally selected from one or more of the compounds sucrose, fructose, glucose, galactose, lactose, maltose, invert sugar, calcium carbonate, lactose, starch, microcrystalline cellulose, lactose monohydrate, calcium hydrogen phosphate, anhydrous calcium hydrogen phosphate, a pharmaceutically acceptable polyol such as xylitol, sorbitol, maltitol, mannitol, isomalt and glycerol, polydextrose, starch, or the like, or any mixture thereof.

Surfactants

In some embodiments, surfactants are used. The use of surfactants as wetting agents in oral drug forms is described in the literature, for example in H. Sucker, P. Fuchs, P. Speiser, Pharmazeutische Technologic, 2nd edition, Thieme 1989, page 260. It is known from other papers, such as published in Advanced Drug Delivery Reviews (1997), 23, pages 163-183, that it is also possible to use surfactants, inter alia, to improve the permeation and bioavailability of pharmaceutical active compounds. Examples of surfactants include, but are not limited to, anionic surfactants, non-ionic surfactants, zwitterionic surfactants and a mixture thereof. Preferably, the surfactants is selected from the group consisting of poly(oxyethylene) sorbitan fatty acid ester, poly (oxyethylene) stearate, poly(oxyethylene) alkyl ether, polyglycolated glyceride, poly(oxyethylene) castor oil, sorbitan fatty acid ester, poloxamer, fatty acid salt, bile salt, alkyl sulfate, lecithin, mixed micelle of bile salt and lecithin, glucose ester vitamin E TPGS (D-α-tocopheryl polyethylene glycol 1000 succinate), sodium lauryl sulfate, and the like, and a mixture thereof.

Glidants

In some embodiments, glidants are used. Examples of glidants which may be used include, but are not limited to, colloidal silicon dioxide, magnesium trisilicate, powdered cellulose, starch, talc and calcium phosphate, or the like, and mixtures thereof.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compound or combination of compounds disclosed herein can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present disclosure may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present disclosure thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds or solids in water-soluble form. In some embodiments, formulations may comprise minocycline and a divalent or trivalent cation (e.g., $Ca^{2+}$, $Mg^{2+}$, $Zn^{2+}$). In various embodiments, the molar ratio of cation to minocycline can be greater than 3:1, 4:1, or 5:1. In some embodiments, the molar ratio is above 5:1. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-fre water, before use.

For oral administration, the compound(s) or combination of compounds disclosed herein can be formulated readily by combining the active compound with pharmaceutically acceptable carriers well known in the art. Such carriers enable the compound or combination of compounds disclosed herein to be formulated as tablets, film coated tablets, pills, dragees, capsules, liquids, gels, get caps, pellets, beads, syrups, slurries, suspensions and the like, for oral ingestion by a patient to be treated. Pharmaceutical preparations for oral use can be obtained by combining the active compound with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. In addition, stabilizers can be added. All formulations for oral administration should be in dosages suitable for such administration. In some embodiments, formulations of the compound(s) or combination of compounds disclosed herein with an acceptable immediate release dissolution profile and a robust, scalable method of manufacture are disclosed.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compound or combination of compounds disclosed herein is conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses arc generally known in the art. Pharmaceutical compositions for intraocular delivery include aqueous ophthalmic solutions of the active compounds in water-soluble form, such as eyedrops, or in gellan gum (Shedden et al., Clin. Ther., 23(3):440-50 (2001)) or hydrogels (Mayer et al., Ophthalmologica, 210(2):101-3 (1996)); ophthalmic ointments; ophthalmic suspensions, such as microparticulates, drug-containing small polymeric particles that are suspended in a liquid carrier medium (Joshi, A., J. Ocul. Pharmacol., 10(1):29-45 (1994)), lipid-soluble formulations (Alm et al., Prog. Clin. Biol. Res., 312:447-58 (1989)), and microspheres (Mordenti, Toxicol. Sci., 52(1):101-6 (1999)); and ocular inserts. All of the above-mentioned references are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, PA (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compound(s) or combination of compounds disclosed herein may also be formulated in rectal compositions such as suppositories or retention enemas, e.g., containing conventional suppository bases such as cocoa butter or other glycerides.

In addition to the formulations described previously, the compound or combination of compounds disclosed herein may also be formulated as a depot preparation. Such long acting formulations may be administered by implantation (for example subcutaneously or intramuscularly) or by intramuscular injection. Thus, for example, the compound or combination of compounds disclosed herein may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol. e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Methods of Administration

The compound(s) or combination of compounds disclosed herein or pharmaceutical compositions may be administered to the patient by any suitable means. Non-limiting examples of methods of administration include, among others, (a) administration though oral pathways, which includes administration in capsule, tablet, granule, spray, syrup, or other such forms; (b) administration through non-oral pathways such as rectal, vaginal, intraurethral, intraocular, intranasal, or intraauricular, which includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrastemally, or the like, including infusion pump delivery: (d) administration locally such as by injection directly in the renal or cardiac area. e.g., by depot implantation; as well as (e) administration topically; as deemed appropriate by those of skill in the art for bringing the compound or combination of compounds disclosed herein into contact with living tissue.

Pharmaceutical compositions suitable for administration include compositions where the compound(s) or combination of compounds disclosed herein is contained in an amount effective to achieve its intended purpose. The therapeutically effective amount of the compound or combination of compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, and the specific use for which the compound or combination of compounds disclosed herein are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

As used herein, a "dosage" refers to the amount of the active pharmaceutical ingredient (e.g., minocycline).

A dose of minocycline provided herein can be from 0.5 mg to 50 mg per kg of body weight, for example from 1 mg to 10 mg per kg of body weight, depending on a number of factors, including the age and sex of the patient, the precise disorder being treated, and its severity. In some embodiments, the dose of minocycline may be greater than 200 mg. For example, in some embodiments, the dose of the minocycline administered may be from about 250 mg to about 1000 mg. In some embodiments, the dose of minocycline may be at least about 300 mg. In some embodiments, the dose of minocycline may be at least about 400 mg. In some embodiments, the dose of minocycline may be at least about 500 mg. In some embodiments, the dose of minocycline may be at least about 600 mg. In some embodiments, the dose of minocycline may be about 250 mg, 300 mg, 350 mg, 400 mg, 450 mg, 500 mg, 550 mg, 600 mg, 650 mg, 700 mg, 750 mg, 800 mg, 850 mg, 900 mg, 950, 1000 mg, or more.

In some embodiments, an initial loading dose of from about 300 mg to 1000 mg minocycline may be administered at the beginning of treatment. In some embodiments, the loading dose may be about 250 mg, 300 mg, 350 mg, 400 mg, 450 mg, 500 mg, 550 mg, 600 mg, 650 mg, 700 mg, 750 mg, 800 mg, 850 mg, 900 mg, 950, 1000 mg, or more minocycline. In some embodiments, from 100 mg to about 600 mg minocycline, for example about 150 mg, 200 mg, 250 mg, 300 mg, 350 mg, 400 mg, 450 mg, 500 mg, 550 mg, or 600 mg, may administered once, twice, or three times daily after the initial loading dose of minocycline.

In some embodiments, the dosing regimen of the compound(s) or combination of compounds disclosed herein is administered for a period of time, which time period can be, for example, from at least about 1 day to at least about 3 days, from at least about 1 day to at least about 1 week, from at least about 1 day to at least about 10 days, from at 1 day to at least about 4 weeks, from at least about 1 week to at least about 2 weeks, from at least about 1 week to at least about 4 weeks, from at least about 4 weeks to at least about 8 weeks, from at least about 4 weeks to at least about 12 weeks, from at least about 4 weeks to at least about 16 weeks, or longer. The dosing regimen of the compound(s) or combination of compounds disclosed herein can be administered three times a day, twice a day, daily, every other day, three times a week, every other week, three times per month, once monthly, substantially continuously or continuously.

Some embodiments provide a method to use an effective amount of minocycline in the treatment of bacterial infection in a subject comprising administering to the subject a dosage of minocycline containing an amount of greater than 200 mg of drug per dose of the compound or combination of compounds disclosed herein, intravenously, three times per month, once monthly, once weekly, once every three days, once every two days, once per day, twice per day, or three times per day substantially continuously or continuously, for the desired duration of treatment.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising the compound or combination of compounds disclosed herein formulated in a compatible pharmaceutical carrier may also be prepared, placed in an appropriate container, and labeled for treatment of an indicated condition.

Preferred subjects for treatment include animals, most preferably mammalian species such as humans, and domestic animals such as dogs, cats and the like, subject to portal hypertension.

Pharmaceutical compositions comprising minocycline disclosed herein capable of treating bacterial infection in an amount effective therefore, and a pharmaceutically acceptable vehicle or diluent are also disclosed. The compositions of the present disclosure may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation or called for by accepted pharmaceutical practice.

The minocycline dosages disclosed herein may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents.

The minocycline disclosed herein, for example, may be administered in a form suitable for immediate release or extended release. Immediate release or extended release may be achieved by the use of suitable pharmaceutical compositions comprising minocycline, or, particularly in the case of extended release, by the use of devices such as subcutaneous implants or osmotic pumps.

The minocycline disclosed herein may also be administered liposomally. For example, the active substance can be utilized in a composition such as tablet, capsule, solution or suspension of minocycline disclosed herein or in topical form for wound healing (0.01 to 5% by minocycline disclosed herein, 1 to 5 treatments per day).

The minocycline disclosed herein may be compounded in a conventional manner with a physiologically acceptable vehicle or carrier, excipient, binder, preservative, stabilizer, flavor, etc., or with a topical carrier.

The minocycline disclosed herein can also be formulated in compositions such as sterile solutions or suspensions for parenteral administration. The minocycline disclosed herein may be compounded with a physiologically acceptable vehicle, carrier, excipient, binder, preservative, stabilizer, etc., in a unit dosage form as called for by accepted pharmaceutical practice. The amount of active substance in these compositions or preparations is preferably such that a suitable dosage in the range indicated is obtained.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. Molded tablets, compressed tablets or freeze-dried tablets are exemplary forms which may be used. Exemplary compositions include those formulating the compound or combination of compounds disclosed herein with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene). For example, the compound or combination of compounds disclosed herein may be administered topically to treat peripheral vascular diseases and as such may be formulated as a cream or ointment.

In some embodiments, the composition disclosed herein can comprise at least 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), or 1.2% (w/w) of a preservative. In some embodiments, the topical composition disclosed herein can comprise 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), 1.2% (w/w), 1.5% (w/w), 2% (w/w), 3% (w/w), 4% (w/w), 5% (w/w), 6% (w/w), 7% (w/w), 8% (w/w), 9% (w/w), 10% (w/w), 20% (w/w) or 30% (w/w) of a preservative or a range defined by any two of the preceding values. In some embodiments, the preservative can include one or more components, two or more components or three or more components.

In some embodiments, the composition disclosed herein can comprise at least 0.1% (w/w), 0.2% (w/w), 0.3% (w/v), 0.4% (w/w), 0.5% (w/w), 0.6% (w/w), 0.7% (w/w), 0.8% (w/w), 0.9% (w/w), 1.0% (w/w), 1.1% (w/w), or 1.2% (w/v) of a preservative including phenoxyethanol, propyl paraben, and methyl paraben. In some embodiments, the topical composition disclosed herein can comprise 0.1% (w/w), 0.2% (w/w), 0.3% (w/w), 0.4% (w/w), 0.5% (w/w), 0.6% (w/w), 0.7% (w/w), 0.8% (w/v), 0.9% (w/w), 1.0% (w/w), 1.1% (w/w), 1.2% (w/w), 1.5% (w/w), 2% (w/w), 3% (w/w), 4% (w/w), 5% (w/w), 6% (w/w), 7% (w/w), 8% (w/w), 9% (w/w), 10% (w/w), 20% (w/w) or 30% (w/w) of a preservative including phenoxyethanol, propyl paraben, and methyl paraben or a range defined by any two of the preceding values.

In some embodiments, the composition may include colorants, deodorants, fragrances, perfumes, anti-foaming agents, lubricants, natural moisturizing agents, skin conditioning agents, skin protectants, skin benefit agents, solvents, solubilizing agents, suspending agents, wetting agents, humectants, propellants, dyes, pigments, and combinations thereof.

In some embodiments, the composition may include additional components added to enhance the odor, texture or color of the composition. For example, fragrances may be added to enhance odor. For example, emulsifiers or inert spheres may be added to enhance texture. For example, colorants may be added to enhance color.

In some embodiments, the composition may be applied to a body portion, such as a hand, foot, knee, elbow, and the like to treat pain and/or inflammation of the body portion. The composition may be applied by any suitable means, such as rubbing, spraying, rolling, wiping, and the like, and massaged into the body portion to be treated.

In some embodiments, the minocycline as disclosed and described herein and/or topical compositions thereof can be used in combination therapy with at least one other agent. In some embodiments, the minocycline disclosed herein and/or topical composition thereof is administered concurrently with the administration of another agent, which may be part of the same topical composition as the compound of the present invention or a different composition. In other embodiments, a topical composition of the present invention is administered prior or subsequent to administration of another agent.

In some embodiments the compositions described herein are incorporated into a patch or film for transdermal drug delivery. In some embodiments, such patches further comprise a porous or resorbable film, an active pharmaceutical agent, and optionally a transdermal carrier or penetration enhancer. Exemplary transdermal carriers include dimethylsulfoxide; 1-dodecylazacycloheptan-2-one or laurocapran;

dimethylacetamide; dimethylformamide: lauric acid: myristic acid; capric acid; caprylic acid; oleic acid; diethylene glycol; tetraethylene glycol; terpenes; essential oils of eucalyptus, chenopodium and ylang-ylang; dimethyl isosorbide; Oxazolidinones such as 4-decyloxazolidin-2-one; 2-pyrrolidone: N-methyl-2-pyrrolidone; urea; EDTA; Sodium Glycolate: polysorbates; sodium deoxycholate; polyethylene glycol; PLA/PLGA nanoparticles: polymer nanoparticles; block-copolymer nanoparticles, especially those comprising Pluronic®-type polyethylene oxide-block-polypropylene oxide copolymers; porous silica nanoparticles; metallic nanoparticles, especially those comprising gold, palladium, and iron; metal oxide nanoparticles, especially those comprising $TiO_2$ and $Al_2O_3$; short chain alcohols such as ethanol, propanol, and butanol; and oils such as mineral oil and coconut oil. In some embodiments the compositions described herein are incorporated into an adhesive for a transdermal patch. In some further embodiments, the compositions described herein are incorporated into a resorbable film. In some embodiments, the active pharmaceutical agent is contained within a separate reservoir layer. In some embodiments, the transdermal patch consists of a single layer. In some embodiments, the transdermal patch is constructed in multiple layers.

Kits

Some embodiments of the present invention include kits comprising minocycline. Some kits include a single use container comprising minocycline. Single use containers include ampules, vials, and the like. The single-use container can comprise a lyophilized formulation of minocycline. Some kits include a diluent for reconstituting the lyophilized formulations of minocycline.

In some embodiments, minocycline may be prepared for single-dosage use. In this embodiment, the solutions of the invention are lyophilized in individual vials such as 20-mL vials. Upon lyophilization, the vials are stoppered with any acceptable stopper. The stoppered vials are then shipped for use. When needed, the vials can be reconstituted by adding sufficient diluents to achieve the desired concentration of minocycline. The concentration of reconstituted solutions may be easily determined by those of ordinary skill in the art. Any pharmaceutically acceptable diluent may be used. Examples of such diluents include but are not limited to water, 0.9% saline. Lactated Ringer's injection solution and dextrose solutions including 5% dextrose (5DW).

In some embodiments, the diluent does not comprise a pharmaceutically acceptable oil (e.g., polyoxyethylene hydrogenated castor oils), a pyridine-containing compound (e.g., nicotinamide), gluconate, an antioxidant, an alcohol (e.g., a polyhydric alcohol, such as, propylene glycol, ethylene glycol), glycerol, polyethylene glycol, a pyrrolidone-containing compound, a water-miscible local anaesthetic (e.g., procaine, tetracaine), urea, lactose, or a dehydrating agent (e.g., ethyl acetate, acetic anhydride, absolute ethanol, ethyl acetate, acetic anhydride, and mixtures thereof). In some embodiments, the diluent does not comprise a tetracycline-solubilizing cosolvent.

In some embodiments, the diluent contains the divalent or trivalent cation. For example, some embodiments include kits that comprise a first container comprising a diluent that comprises an aqueous solution of a divalent or trivalent cation; and a second container comprising a solid composition soluble in the diluent, wherein the solid composition comprises minocycline in an amount such that the molar ratio of the divalent or trivalent cation to minocycline is greater than about 2:1. In some embodiments, the diluent comprises an acid, e.g., HCL. In some embodiments, the diluent comprises a buffer. In some embodiments, the buffer is sodium acetate.

More embodiments include kits comprising a first container comprising a diluent that comprises an aqueous solution of a divalent or trivalent cation; and a second container comprising a solid composition soluble in the diluent, wherein the solid composition comprises minocycline in an amount such that the molar ratio of the divalent or trivalent cation to minocycline is greater than 3:1.

More embodiments include single use vials comprising any composition wherein the vial comprises an amount of minocycline of at least 100 µg 200 µg, 300 µg, 400 µg, 500 µg, 600 µg, 700 µg, 800 µg, 900 µg, 1000 µg. In some embodiments, the vial comprises an amount of minocycline of at least 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, and 130 mg. In some embodiments, the vial comprises an amount of minocycline of at least 100 mg, 200 mg, 300 mg, 400 mg, 500 mg, and 600 mg. In some embodiments, the vial comprises about 1000 mg of minocycline. In some embodiments, the vial comprises about 300 mg of minocycline. In some embodiments, the vial comprises about 400 mg of minocycline. In some embodiments, the vial comprises about 500 mg of minocycline. In some embodiments, the vial comprises about 600 mg of minocycline.

EXAMPLE

Embodiments of the present application are disclosed in further detail in the following example, which is not in any way intended to limit the scope of the present disclosure.

Example 1

This example describes outcomes among healthy adult subjects in a randomized, double-blind, placebo-controlled, single- and multiple ascending dose (SAD/MAD) study of 6 intravenous doses (cohorts) ranging from 100 mg to 600 mg of minocycline. Each cohort consisted of 10 subjects (8 active drug and 2 placebo). Within each cohort, subjects received a single dose on Day 1, followed by a loading dose on Day 4, then 7 days of twice-daily dosing (Days 4-10), followed by a single dose on Day 11 as shown in Table 1. Within each cohort, subjects were randomly assigned to minocycline (n=8) or normal saline placebo (n=2). Serial blood and urine samples were collected for pharmacokinetic assessment.

TABLE 1

Dosing of cohorts in SAD/MAD study

| Cohort | Single Dose (mg) Day 1 | Loading Dose (mg) Day 4 | Repeated Doses (mg) Days 4-11 |
|---|---|---|---|
| 1 | 100 | 100 | 100 |
| 2 | 200 | 200 | 200 |
| 3 | 300 | 300 | 300 |
| 4 | 400 | 400 | 400 |
| 5 | 500 | 500 | 300 |
| 6 | 600 | 600 | 300 |

Figure 2:
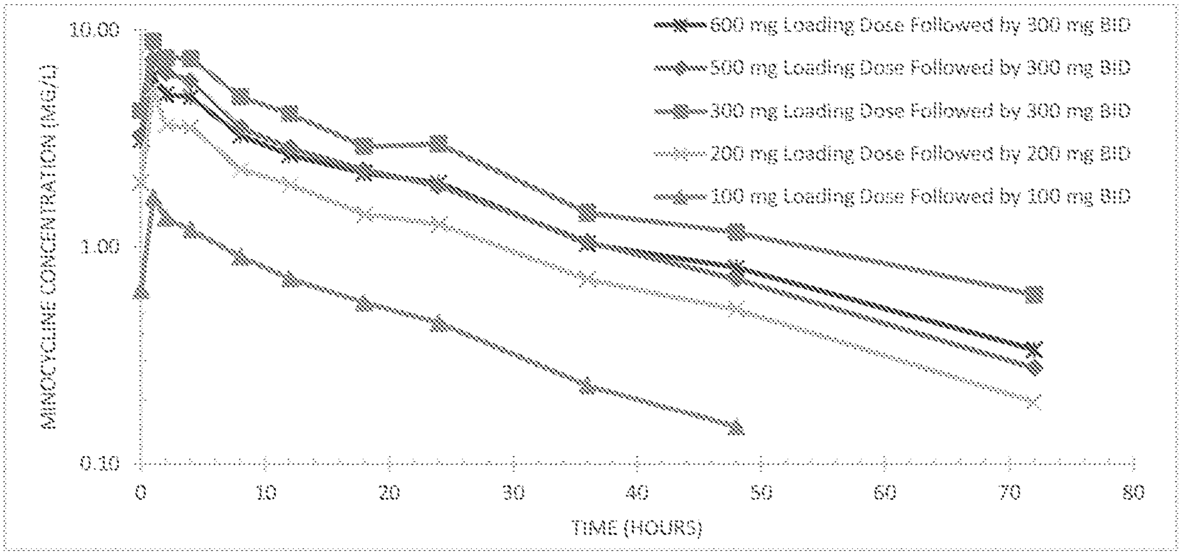
FIG. 2 shows plasma pharmacokinetics of minocycline in healthy volunteers after a loading dose then twice daily dosing for 7 days.

All infusions were administered over 1 hour. Plasma samples were obtained at 1 (end-of-infusion), 2, 4, 8, 12, 18, 24, 36, 48, and 72 hours after the start of dosing after single or multiple doses and assayed for minocycline content using a validated HPLC/MS method. Concentration of minocycline in healthy volunteers after a one hour IV infusion is shown in FIG. 1, while concentration of minocycline in healthy volunteers after a loading dose then twice daily dosing for seven days is shown in FIG. 2.

Sixty-nine subjects were randomized: 91.3% white, mean age 28.1 years, mean Body Mass Index (BMI) of 22.8 kg/m$^2$ and mean estimated glomerular filtration rate (eGFR) of 103.0 mL/min/1.73 m$^2$. Patient demographics are provided in Table 2. No serious adverse events occurred. Fifty-fine (79.9%) reported study drug related adverse events: 41 (59.4%) dizziness, 35 (50.7%) nausea, including 9 with moderate nausea and/or dizziness. All other adverse events were of mild intensity. After 6 subjects in the 400 mg cohort were discontinued from study drug use due to nausea and dizziness, MAD escalation was stopped. Subsequent cohorts were escalated from SAD and loading dose only. The results of the single ascending dose study are shown in Table 3 and the results of the multiple ascending dose study are shown in Table 4.

TABLE 2

Baseline Demographics

| Cohort | | 1 | 2 | 3 | 4 | 5 | 6 | Placebo | Total |
|---|---|---|---|---|---|---|---|---|---|
| Age, years | Mean | 26.6 | 31.0 | 25.0 | 29.6 | 25.8 | 30.6 | 27.4 | 28.1 |
| | SD | 7.8 | 7.5 | 7.5 | 8.7 | 8.8 | 12.1 | 8.2 | 8.7 |
| Race: White | N | 8 | 7 | 8 | 7 | 6 | 7 | 14 | 57 |
| | % | 100.0 | 87.5 | 100.0 | 87.5 | 75.0 | 77.8 | 100.0 | 91.3 |
| Race: Black | N | | 1 | | | 2 | 1 | | 4 |
| or African American | % | | 12.5 | | | 25.0 | 11.1 | | 5.8 |
| Race: Asian | N | | | | 1 | | 1 | | 2 |
| | % | | | | 12.5 | | 11.1 | | 2.9 |
| Sex: Male | N | 5 | 5 | 6 | 5 | 6 | 5 | 7 | 44 |
| | % | 62.5 | 62.5 | 75.0 | 62.5 | 75.0 | 55.6 | 50.0 | 63.8 |
| Sex: Female | N | 3 | 3 | 2 | 3 | 2 | 4 | 7 | 25 |
| | % | 37.5 | 37.5 | 25.0 | 37.5 | 25.0 | 44.4 | 50.0 | 36.2 |
| Height, cm | Mean | 179.3 | 175.8 | 178.1 | 175.4 | 178.0 | 176.4 | 178.1 | 177.7 |
| | SD | 9.8 | 7.6 | 7.1 | 9.2 | 6.0 | 11.0 | 10.1 | 8.9 |
| Weight, kg | Mean | 75.1 | 71.7 | 71.6 | 69.9 | 72.6 | 73.0 | 70.9 | 72.1 |
| | SD | 10.6 | 9.0 | 10.1 | 11.6 | 8.0 | 12.7 | 14.6 | 11.0 |
| BMI, kg/m$^2$ | Mean | 23.3 | 23.2 | 22.5 | 22.7 | 22.9 | 23.4 | 22.1 | 22.8 |
| | SD | 2.6 | 2.7 | 2.4 | 2.9 | 2.5 | 3.0 | 2.8 | 2.7 |

TABLE 3

Pharmacokinetics of minocycline in the single ascending dose (SAD) phase

| Dose (mg) | 100 | 200 | 300 | 400 | 500 | 600 |
|---|---|---|---|---|---|---|
| N | 8 | 8 | 8 | 8 | 8 | 9 |
| $C_{max}$ | 0.99 | 1.89 | 3.35 | 4.93 | 4.36 | 7.03 |
| (mg/mL) | (0.2) | (0.4) | (1.2) | (1.8) | (0.9) | (2.4) |
| $T_{1/2}$ | 11.05 | 13.70 | 16.62 | 17.55 | 14.44 | 17.27 |
| (h) | (2.1) | (2.3) | (3.9) | (2.1) | (2.7) | (3.6) |
| $AUC_{0-\infty}$ | 9.73 | 25.90 | 39.16 | 63.64 | 53.76 | 83.00 |
| (mg*h/L) | (1.4) | (6.9) | (13.8) | (18.2) | (20.3) | (29.4) |
| Cl | 10.48 | 8.21 | 8.28 | 6.71 | 10.25 | 8.07 |
| (L/h) | (1.8) | (2.2) | (2.1) | (1.7) | (3.0) | (2.8) |
| $V_{ss}$ | 156 | 148 | 158 | 142 | 179 | 153 |
| (L) | (36.7) | (36.6) | (45.4) | (38.0) | (46.5) | (52.8) |

AUC = area under the drug concentration-time curve; $C_{max}$ = maximum observed drug concentration; $T_{1/2}$ = half-life; Cl = plasma clearance; $V_{ss}$ = volume of distribution at steady state.

TABLE 4

Pharmacokinetics of minocycline in the twice-daily ascending dose (MAD) phase

| | Single Dose (mg) | | | | | |
|---|---|---|---|---|---|---|
| | 100 | 200 | 300 | 500 | 600 | 300, 500, or 600 |
| | BID Dosing (mg) | | | | | |
| | 100 | 200 | 300 | 300 | 300 | 300 |
| N | 6 | 6 | 7 | 7 | 4 | 18 |
| $C_{max}$ | 1.71 | 4.59 | 8.91 | 7.58 | 6.17 | 7.79 |
| (mg/L) | (0.2) | (1.1) | (4.5) | (2.4) | (1.7) | (3.3) |
| $T_{1/2}$ | 15.89 | 18.22 | 19.78 | 18.15 | 20.19 | 19.24 |
| (h) | (2.8) | (2.4) | (3.4) | (1.4) | (4.2) | (2.9) |
| $AUC_{0-t}$ | 27.5 | 80.7 | 173.7 | 124.1 | 119.0 | 142.3 |
| (mg*h/L) | (5.5) | (19.9) | (100.8) | (50.2) | (56.3) | (75.6) |
| Cl | 3.49 | 2.48 | 1.92 | 2.64 | 2.79 | 2.39 |
| (L/h) | (0.7) | (0.8) | (0.7) | (1.1) | (1.3) | (1.0) |
| $V_{ss}$ | 72.05 | 58.42 | 47.05 | 58.06 | 67.81 | 55.94 |
| (L) | (9.3) | (15.7) | (14.0) | (20.1) | (24.4) | (19.6) |

AUC = area under the drug concentration-time curve; $C_{max}$ = maximum observed drug concentration; $T_{1/2}$ = half-life; Cl = plasma clearance; $V_{ss}$ = volume of distribution at steady state.

Single intravenous doses of minocycline up to 600 mg were tolerated reasonably well, but the maximum tolerated multi-dose was 300 mg administered twice daily. Most common adverse effects were mild nausea and dizziness. Exposure increased in a dose proportional fashion with exception of the 500 mg dose.

Safety was assessed throughout the study. Of the adverse events (AE) observed in more than 10% of subjects, the vast majority were assessed by the investigator as likely to be related to study drug (Table 5). A total of 21 subjects out of 57 discontinued the trial. Six of 10 subjects in cohort 4 discontinued during the MAD portion (400 mg BID) of the trial due to mild to moderate dizziness. Dosing was discontinued in the remaining 4 subjects in that cohort and cohorts 5 and 6 were limited to 300 mg BID for the MAD portion of the trial. Four subjects in cohort 6 (600 mg/300 mg) discontinued due to nausea. No serious adverse events (SAEs) were reported.

TABLE 5

Related Adverse Events (incidence >10%)

| Cohort | | 1 | 2 | 3 | 4 | 5 | 6 | Pooled Placebo | Total |
|---|---|---|---|---|---|---|---|---|---|
| Dose (mg) | | 100 | 200 | 300 | 400 300* | 500/ 300^ | 600/ | | |
| N Total | | 8 | 8 | 8 | 8 | 8 | 9 | 12 | 61 |
| | | | | Overall | | | | | |
| Subjects with any related AE | N | 6 | 8 | 8 | 8 | 8 | 9 | 4 | 51 |
| | % | 75.0 | 100.0 | 100.0 | 100.0 | 100.0 | 100.0 | 33.3 | 83.6 |
| Dizziness | N | 1 | 4 | 8 | 8 | 8 | 7 | 3 | 39 |
| | % | 12.5 | 50.0 | 100.0 | 100.0 | 100.0 | 77.8 | 16.7 | 62.0 |
| Nausea | N | 2 | 6 | 6 | 5 | 6 | 8 | 1 | 34 |
| | % | 25.0 | 75.0 | 75.0 | 62.5 | 75.0 | 88.9 | 8.3 | 55.7 |
| Infusion site reaction | N | 5 | 7 | 7 | 1 | 6 | 6 | 0 | 32 |
| | % | 62.5 | 87.5 | 87.5 | 12.5 | 75.0 | 66.7 | 0.0 | 52.5 |
| Headache | N | 1 | 4 | 0 | 3 | 4 | 5 | 1 | 18 |
| | % | 12.5 | 50.0 | 0.0 | 37.5 | 50.0 | 55.6 | 8.3 | 29.5 |
| Dysgeusia | N | 0 | 0 | 0 | 4 | 4 | 6 | 3 | 17 |
| | % | 0.0 | 0.0 | 0.0 | 50.0 | 50.0 | 66.7 | 25.0 | 27.9 |
| Decreased appetite | N | 1 | 3 | 2 | 2 | 3 | 0 | 1 | 12 |
| | % | 12.5 | 37.5 | 25.0 | 25.0 | 37.5 | 0.0 | 8.3 | 19.7 |
| Vomiting | N | 0 | 2 | 2 | 0 | 1 | 3 | 0 | 8 |
| | % | 0.0 | 25.0 | 25.0 | 0.0 | 12.5 | 33.3 | 0.0 | 13.1 |

*Single dose (day 1) and loading dose ($1^{st}$ dose day 4): 500 mg; subsequent doses: 300 mg
^Single dose (day 1) and loading dose ($1^{st}$ dose day 4): 600 mg; subsequent doses: 300 mg Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method of treating one or more bacterial infection in a subject, wherein the infection is carbapenem-resistant, comprising, in a period of 1 day, intravenously administering minocycline to the subject in need thereof a loading dose of 600 mg and a single dose of from 250 mg to 1000 mg following the loading dose.

2. The method of claim 1, wherein the bacterial infection is selected from the group consisting of *Escherichia coli, Klebsiella pneumoniae, Pseudomonas aeruginosa, Enterobacter cloacae* species complex, *Enterococcus faecium, Serratia marcescens, Streptococcus pyogenes, Streptococcus pneumoniae, Haemophilus influenzae, Chlamydia trachomatis, Mycoplasma pneumoniae, Legionella pneumophila, Acinetobacter baumannii, Bartonella bacilliformis, Brucella* species, *Calymmatobacterium granulomatis, Campylobacter fetus, Francisella tularensis, Haemophilus ducreyi, Vibrio cholerae*, and *Yersinia pestis.*

3. The method of claim 2, wherein the bacterial infection is *Acinetobacter baumannii.*

4. The method of claim 1, wherein the single dose of minocycline is from 300 mg to 1000 mg.

5. The method of claim 1, wherein the single dose of minocycline is from 400 mg to 1000 mg.

6. The method of claim 1, wherein the single dose of minocycline is from 500 mg to 1000 mg.

7. The method of claim 1, wherein the single dose of minocycline is from 600 mg to 1000 mg.

8. The method of claim 1 wherein the single dose of minocycline is administered two times daily.

9. The method of claim 1 wherein the single dose of minocycline is administered three times daily.

10. The method of claim 1, wherein the minocycline is administered from about 1 day to at least about 4 weeks.

11. The method of claim 1, wherein the single dose of minocycline is intravenously administered over a one hour infusion period.

* * * * *